United States Patent
Bombardelli et al.

(10) Patent No.: US 7,053,222 B2
(45) Date of Patent: May 30, 2006

(54) SEMI-SYNTHETIC PROCESS FOR THE PREPARATION OF N-DEBENZOYLPACLITAXEL

(75) Inventors: Ezio Bombardelli, Milan (IT); Gabriele Fontana, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 10/961,044

(22) Filed: Oct. 12, 2004

(65) Prior Publication Data

US 2005/0049297 A1    Mar. 3, 2005

Related U.S. Application Data

(63) Continuation-in-part of application No. PCT/EP03/03017, filed on Mar. 24, 2003.

(30) Foreign Application Priority Data

Apr. 12, 2002  (IT)  ............ MI2002A0782

(51) Int. Cl.
C07D 263/04 (2006.01)
C07D 305/14 (2006.01)
C07C 321/28 (2006.01)

(52) U.S. Cl. ............ 548/215; 549/510; 549/511; 562/431

(58) Field of Classification Search ............ 549/510, 549/511; 548/215; 562/431
See application file for complete search history.

(56) References Cited

FOREIGN PATENT DOCUMENTS

| WO | 97/42167 | 11/1997 |
|----|----------|---------|
| WO | 98/08833 | 3/1998  |

*Primary Examiner*—Bernard Dentz
(74) *Attorney, Agent, or Firm*—Young & Thompson

(57) ABSTRACT

A process for the preparation of N-debenzoylpaclitaxel (I) through esterification of 7-protected baccatin III with a carboxylic acid reactive derivative of general formula (II), and elimination of the ester-protecting groups in acid conditions and in a single step. In formula (II) R1 is aryl or heteroaryl. The compound of formula (I) can be conveniently used for the preparation of paclitaxel and analogues

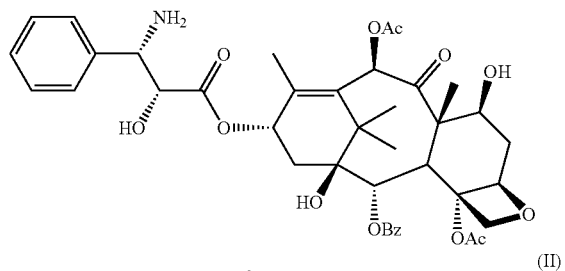

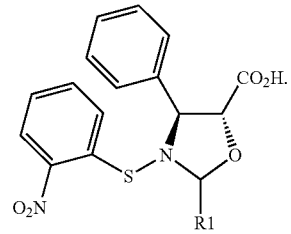

13 Claims, No Drawings

SEMI-SYNTHETIC PROCESS FOR THE PREPARATION OF N-DEBENZOYLPACLITAXEL

CROSS REFERENCE TO RELATED APPLICATIONS

This application is a continuation-in-part of international application PCT/EP03/03017 filed on 24 Mar. 2003, which designated the United States of America. International application PCT/EP03/03017 claimed priority to earlier Italian application MI2002 A 000782 filed on 12 Apr. 2002.

FIELD OF THE INVENTION

The present invention relates to a process for the preparation of N-debenzoylpaclitaxel (I)

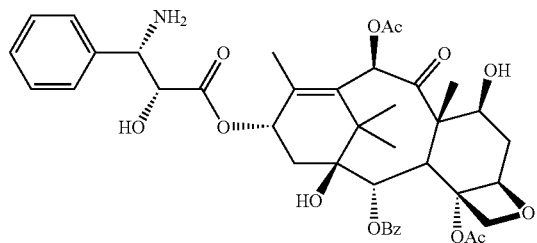

(I)

which is a useful precursor for known molecules having antitumor activity.

SUMMARY OF THE INVENTION

According to present invention, the derivative of formula (I) is obtained by condensation of an oxazolidine of general formula (II) or of a reactive derivative thereof

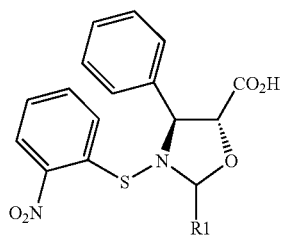

(II)

in which R1 is an aryl or heteroaryl group, with a baccatin derivative of general formula (III)

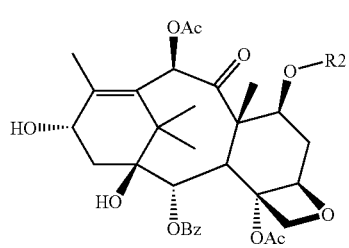

(III)

in which R2 is a hydroxy-protecting group removable by acid-catalyzed solvolysis, to give a compound of general formula (IV)

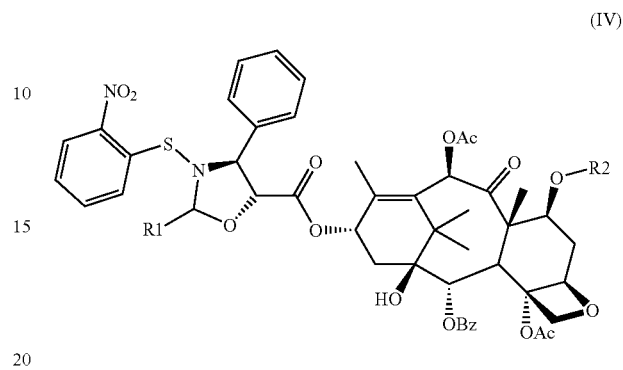

(IV)

in which R1 and R2 are as defined above, which compound is subjected to controlled acidic conditions to afford in a single step the compound of formula (I), an useful intermediate for the preparation of known antitumor compounds.

The present invention is advantageous over the synthetic processes of the prior art, in that:

the oxazolidine of general formula (II) is surprisingly enriched in one of the epimers at C 2;

all the nitrogen- and oxygen-protecting groups are simultaneously removed by simple solvolysis;

the reaction conditions minimize the formation of isomerization or degradation products.

R1 is preferably phenyl or phenyl substituted with one or more $C_1$–$C_3$ alkoxy, halogen, $C_1$–$C_3$ alkyl, halogen-$C_1$–$C_2$ alkyl groups. More preferably, R1 is 2,4-dimethoxyphenyl.

R2 can be any hydroxy-protecting group which can be removed by acid-catalyzed solvolysis. Examples of suitable protective groups are acetals (particularly methoxypropyl), alkoxycarbonyls (such as t-butoxycarbonyl), sulfenyl derivatives (such as 2-nitrobenzenesulfenyl). Particularly preferred is the protection with the 2-nitrobenzenesulfenyl group.

DETAILED DESCRIPTION OF THE INVENTION

According to present invention, the baccatin derivative of general formula (III) is esterified with an acid, salt or reactive derivative of general formula (II) in the presence of a condensing agent, for example a carbodiimide such as cyclohexylcarbodiimide or 1-(3-dimethylaminopropyl)-3-ethylcarbodiimide and an activating agent such as 4-dimethylaminopyridine or N-methylimidazole, in organic solvents selected from ethers (particularly tetrahydrofuran), hydrocarbons (such as toluene or hexane), halogenated hydrocarbons (particularly dichloromethane), or mixtures thereof at temperatures ranging from 0 to 90° C. It is particularly advantageous to carry out the reaction in toluene and dichloromethane at a temperature of about 70° C.

Among the acid derivatives of formula (II), particularly preferred is the use of an ammonium salt of formula (V)

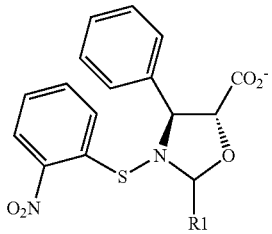 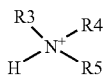

(V)

wherein R1 is as defined above and R3, R4 and R5, which can be the same or different, are a $C_1$–$C_6$ alkyl group, in particular ethyl, aryl or arylalkyl, preferably benzyl. The use of the ammonium salt provides less drastic reaction conditions and better stability of the products involved.

In principle, any activated carboxylic acid derivative (III), such as mixed anhydrides, acyl halides, pentafluorophenyl ester, thioesters, can be used in the process of the invention according to known procedures.

The oxygen- and nitrogen-protecting groups are removed in a single step by acid-catalyzed solvolysis, preferably by treatment with methanol and p-toluenesulfonic acid, at a temperature ranging from −20 to 50° C.

The acid of formula (II) can be obtained by hydrolysis of an ester of formula (VI)

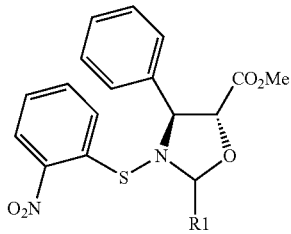

(VI)

to give a salt of formula (VII)

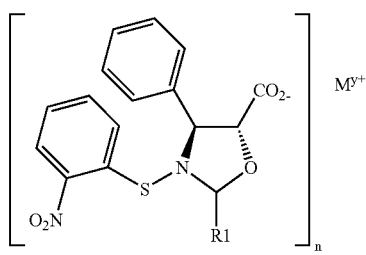

(VII)

wherein M is a metal having y charge ranging from 1 to 2 and n is an integer always equal to y.

The hydrolysis is usually carried out in alkali medium by means of inorganic bases, such as metal hydroxides or metal carbonates, in a water-alcoholic medium at a temperature ranging from 0 to 40° C.

The triethylammonium salts of formula (VIII)

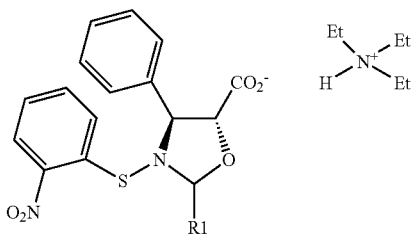

(VIII)

can be obtained by treating the salts of formula (VII) with a triethylammonium chloride methanolic solution in a wide range of temperatures.

The ester (VI) in which R1 is 2,4-dimethoxyphenyl can be obtained by reacting 2,4-dimethoxybenzaldehyde dimethylacetal (X) with N-(2-nitrobenzenesulfenyl)-3-phenylisoserine of formula (IX)

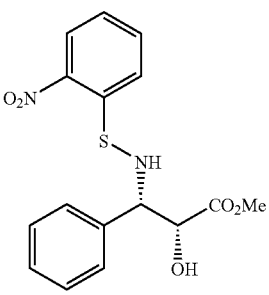

(IX)

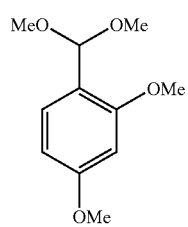

(X)

in an inert organic solvent, or in mixtures of inert organic solvents, in the presence of a mild acid catalyst such as pyridinium p-toluenesulfonate at a temperature ranging from 0° C. to the boiling temperature of the mixture. Suitable solvents are aromatic hydrocarbons.

The compound of formula (IX) can be prepared by reacting 3-phenylisoserine hydrochloride methyl ester with 2-nitrobenzenesulfenyl chloride in a diphasic mixture consisting of a water-immiscibile inert organic solvent (preferably ethyl acetate or dichloromethane) and an aqueous basic buffer (such as a sodium bicarbonate saturated solution) at temperatures ranging from 4 to 50° C.

7-(2-Nitrobenzenesulfenyl)-baccatin III can be easily prepared by reacting baccatin III with 2-nitrobenzenesulfenyl chloride in inert solvents, particularly ethers or halogenated hydrocarbons, in the presence of an organic or inorganic base, at temperatures ranging from −10 to 40° C.

The compounds:
7-(2-nitrobenzenesulfenyl)-baccatin III;
13-[N-(2-nitrobenzenesulfenyl)-N,O-(2,4-dimethoxybenzylidene)-3-phenylisoserinoyl]-7-(2-nitrobenzenesulfenyl)-baccatin III;

2-(2,4-dimethoxyphenyl)-3-(2-nitrobenzenesulfenyl)-4-phenyl-5-oxazo-lidinecarboxylic acid and the salts and C1–C3 alkyl esters thereof, in particular the sodium and triethylammonium salts and the methyl ester;

N-(2-nitrobenzenesulfenyl)-3-phenylisoserine, are novel, useful intermediates and are a further object of the invention.

The following examples illustrate the invention in greater detail.

EXAMPLES

Example I

N-(2-nitrobenzenesulfenyl)-3-phenylisoserine 5 g of phenylisoserine methyl ester dissolved in 100 ml of ethyl acetate and 130 ml of a saturated NaHCO$_3$ solution are mixed in a 500-ml round-bottom flask. The diphasic mixture is kept under vigorous stirring and 5 g of 2-nitrobenzenesulfenyl chloride are added thereto in 30 minutes. The mixture is left under stirring for 30 min, then the organic phase is separated, dried over sodium sulfate and evaporated under reduced pressure. The residual yellow oil is purified by chromatography (silica,hexane-ethyl acetate, gradient 25 to 50% ethyl acetate) to give the desired product in 74% yield.

Example II 2-(2,4-dimethoxyphenyl)-3-(2-nitrobenzenesulfenyl)-4-phenyl-5-oxazolidinecarboxylic acid methyl ester A hot solution of 6.6 g N-(2-nitrobenzenesulfenyl)-3-phenylisoserine in 100 ml of dry benzene is added with 0.5 g of pyridinium p-toluenesulfonate and 5.3 g of 2,4-dimethoxybenzaldehyde dimethylacetal. The solution is refluxed for 4 hours, then left to cool to room temperature. After that, 10 ml of a NaHCO$_3$ saturated solution are added and the phases are separated. The aqueous phase is extracted with ethyl acetate and the combined organic phases are dried over Na$_2$SO$_4$ and evaporated under reduced pressure. The residual yellow oil is purified by chromatography (silica, hexane-ethyl acetate 5:1 with 2% triethylamine) to give the desired product in 74% yield.

Example III

Sodium 2-(2,4-dimethoxyphenyl)-3-(2-nitrobenzene-sulfenyl)-4-phenyl-5-oxazolidinecarboxylate A solution of 5 g of 2-(2,4-dimethoxyphenyl)-3-(2-nitrobenzenesulfenyl)-4-phenyl-5-oxazolidinecarboxylic acid methyl ester in 150 ml of methanol are added with 22 ml of 2% sodium hydroxide. The mixture is refluxed for 1 hour. The solvent is distilled off and the residue is dried at 40° C. under vacuum overnight.

Example IV

Triethylammonium 2-(2,4-dimethoxyphenyl)-3-(2-nitrobenzenesulfenyl)-4-phenyl-5-oxazolidinecarboxylate A solution of 13 mmol of the salt described above in 20 ml of dry methanol is added with 1.83 g of triethylammonium chloride. The mixture is kept under stirring for 3 hours, then diluted with 150 ml of toluene. The resulting suspension is filtered with suction and the mother liquors are evaporated to give the desired product in almost quantitative yield. The product is used without further purification.

Example V 7-(2-nitrobenzenesulfenyl)-baccatin III 8.8 g of baccatin III and 3.13 g of 2-nitrobenzenesulfenyl chloride are dissolved in 100 ml of dry methylene chloride in a 500-ml round-bottom flask. After cooling the solution at 0° C., 5 ml of pyridine are dropped therein at such a rate as to keep temperature below 5° C. The mixture is then kept under stirring at 0° C. for 30 min, then diluted with 50 ml of methylene chloride and washed with 5% NaHCO$_3$ and then with brine. After drying over magnesium sulfate, the organic phase is evaporated under reduced pressure. The resulting crude is purified by chromatography (silica,hexane-ethyl acetate 6:4) to give 5.4 g of the desired product.

Example VI

13-[N-(2-nitrobenzenesulfenyl)-N,O-(2,4-dimethoxy-benzylidene)-3-phenylisoserinoyl]-7-(2-nitrobenzenesulfenyl)-baccatin III A mixture of 2.9 g of 7-(2-nitrobenzenesulfenyl)-baccatin III, 2.9 g of triethylammonium 2-(2,4-dimethoxyphenyl)-3-(2-nitrobenzenesulfenyl)-4-phenyl-5-oxazolidinecarboxylate in 15 ml of methylene chloride and 30 ml of dry toluene, is added with 1.5 g of dicyclohexylcarbodiimide and 0.24 g of 4-dimethylaminopyridine. The reaction mixture is refluxed for 2 hours, then left under stirring at room temperature overnight. The organic phase is filtered with suction, then washed with 30 ml of saturated sodium hydrogen carbonate, then with brine and evaporated under reduced pressure. The residue is purified by chromatography (silica, hexane-ethyl acetate 7:3) to give the desired product in 75% yield.

Example VII

N-debenzoylpaclitaxel 4.4 g of 13-[N-(2-nitrobenzenesulfenyl)-N,O-(2,4-dimethoxybenzylidene)-3-phenylisoserinoyl]-7-(2-nitrobenzenesulfenyl)-baccatin III and 1.4 g of p-toluenesulfonic acid are dissolved in 15 ml of dry methanol at 0° C. The solution is left under stirring at 0° C. for 3–8 hours. The reaction is monitored by TLC. 15 ml of a sodium bicarbonate saturated solution are then added, the solvent is evaporated off and the residue is dissolved in ethyl acetate. The organic layer is washed with water and dried over Na$_2$SO$_4$. Evaporation of the solvent and purification on a column (methylene chloride-methanol 95:5) give the desired product in 80% yield.

Example VIII

N-debenzoylplaclitaxel 4.4 g of 13-[N-2-nitrobenzenesulfenyl)-N,O-(2,4-dimethoxybenzylidene)-3-phenylisoserinoyl]-7-2-nitrobenzenesulfenyl)-baccatin III was dissolved in a mixture of CH$_2$Cl$_2$ (16 mL), MeOH (8 ml) and Pyridine (4 ml). To the solution was added dropwise 12 N HCl (2 ml) and the reaction was left under stirring for an hour. After an hour, additional 3.4 ml of 12 N HCl were added dropwise and the reaction mixture was kept under stirring at 35° C. for another hour. CH₂Cl₂ (25 ml) was added to the solution and a washing of the organic solution with HCl 1 M (1×20 ml) was performed.

The organic layer was evaporated to dryness and the residue, redissolved in CH₂Cl₂ (30 ml), was precipitated by pouring into 500 ml of toluene. After filtration and dryness under vacuum at 50° C., 2.3 g of N-debenzoyl placitaxel as hydrochloride salt were obtained (yeld: 80%).

What is claimed is:

1. A process for the preparation of N-debenzoylpaclitaxel (I)

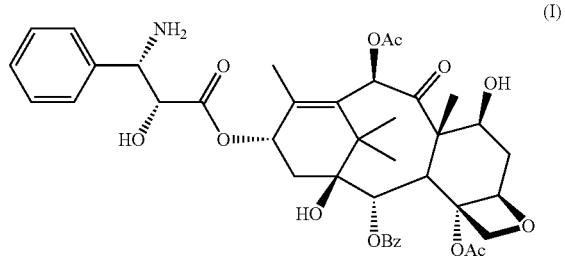

which comprises:

(a) condensing a carboxylic acid of formula (II), or a salt or an activated derivative thereof

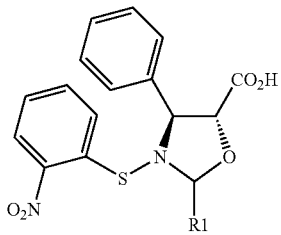

in which R1 is an aryl or heteroaryl group, with a baccatin derivative of formula (III)

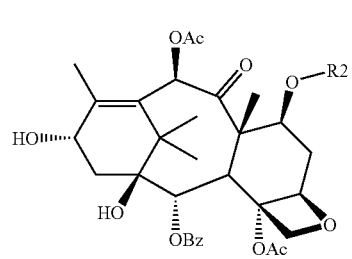

in which R2 is a hydroxy-protecting group removable by acid-catalyzed solvolysis, to give a compound of formula (IV)

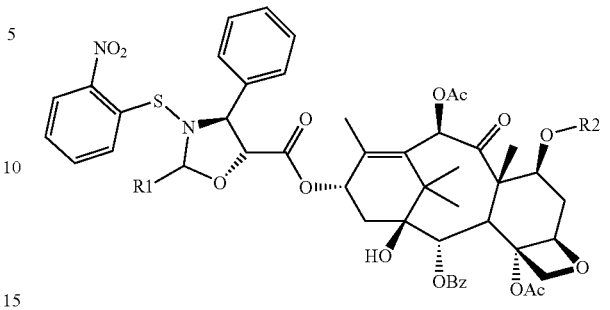

in which R1 and R2 are as defined above;

b) removing the R2 group and opening the oxazolidine ring in the compound of formula (IV) by acid-catalyzed solvolysis.

2. A process as claimed in claim 1 wherein R1 is 2,4-dimethoxyphenyl and R2 is 2-nitrobenzenesulfenyl.

3. A process as claimed in claim 1 in which step a) is carried out in the presence of a condensing agent and of an activating agent in organic solvents selected from ethers, hydrocarbons, halogenated hydrocarbons, or mixtures thereof at temperatures ranging from 0 to 90° C.

4. A process as claimed in claim 3 in which the solvent is a mixture of toluene and dichloromethane and the reaction temperature is approx. 70° C.

5. A process as claimed in claim 1 in which compound (III) is reacted with an ammonium salt of formula (V)

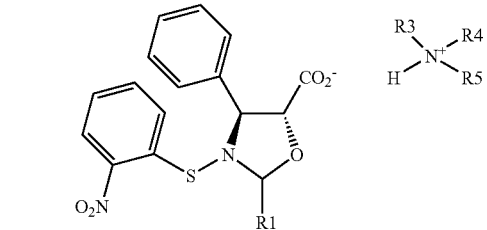

wherein R1 is as defined above and R3, R4 and R5 are a C1–C6 alkyl, aryl or arylalkyl group.

6. A process as claimed in claim 1 in which the oxygen- and nitrogen-protecting groups are removed in a single step by treatment with methanol and p-toluenesulfonic acid, at a temperature ranging from −20 to 50° C.

7. A process for preparing compounds of formula (II)

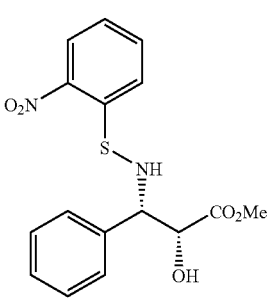

said process comprising:

a) preparation of the N-(2-nitrobenzenesulfenyl)-3-phenylisoserine methyl ester of formula (IX);

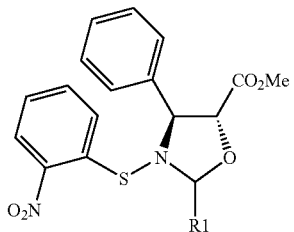

(VI)

b) treatment of compound (IX) with an aldehyde dimethylacetal to give a compound of formula (VI)

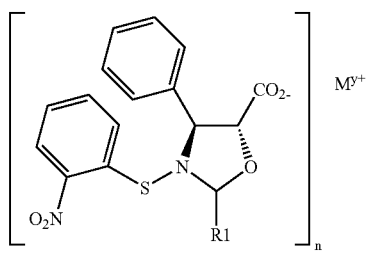

(VII)

in which R1 is an aryl or heteroaryl group;

c) hydrolysis of the ester of formula (VI) to give a salt of formula (VII)

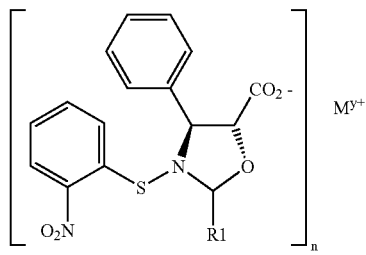

(VII)

wherein R1 is an aryl or heteroaryl group, M is a metal with y positive charge ranging from 1 to 2, and n is an integer which is always equal to y;

d) acidification of the salt of formula (VII) to give the compound of formula (II).

8. A process as claimed in claim 7 in which the hydrolysis is carried out in alkali medium by means of metal hydroxides or metal carbonates in a water-alcoholic medium at a temperature ranging from 0 to 40° C.

9. A process as claimed in claim 7 in which step b) is carried out by heating compound (IX) with 2,4-dimethoxybenzaldehyde dimethylacetal in an inert organic solvent, or in mixtures of inert organic solvents, in the presence of a mild acid catalyst, at a temperature ranging from 0° C. to the boiling temperature of the mixture.

10. A process for preparing a compound of formula (V)

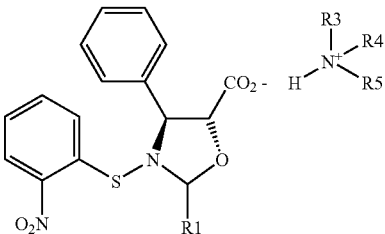

(V)

in which R3, R4 and R5 are ethyl, by treatment of a compound of formula (VII)

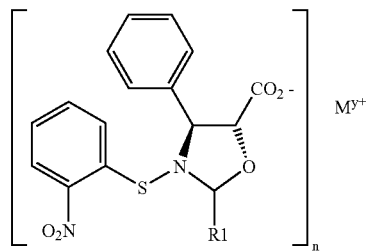

(VII)

in which M is sodium, with a triethylammonium chloride methanolic solution.

11. A compound selected from:
   7-(2-nitrobenzenesulfenyl)-baccatin III;
   13[N-(2-nitrobenzenesulfenyl)-N,O-(2,4-dimethoxybenzylidene)-3-phenylisoserinoyl]-7-(2-nitrobenzenesulfenyl)-baccatin III;
   2-(2,4-dimethoxyphenyl)-3-(2-nitrobenzenesulfenyl)-4-phenyl-5-oxazolidinecarboxylic acid and the salts and C1–C3 alkyl esters thereof;
   N-(2nitrobenzenesulfenyl)-3-phenylisoserine.

12. A process as claimed in claim 2 in which step a) is carried out in the presence of a condensing agent and of an activating agent in organic solvents selected from ethers, hydrocarbons, halogenated hydrocarbons, or mixtures thereof at temperatures ranging from 0 to 90° C.

13. A process as claimed in claim 12 in which the solvent is a mixture of toluene and dichloromethane and the reaction temperature is approx. 70° C.

* * * * *